(12) United States Patent
Martin et al.

(10) Patent No.: US 6,456,418 B1
(45) Date of Patent: Sep. 24, 2002

(54) FLEXIBLE ELECTROCHROMIC DEVICES

(75) Inventors: Paul James Martin; Marie Di Pasquale, both of Gloucester City, NJ (US)

(73) Assignee: Chameleon Optics, INC, Philadelphia, PA (US)

( * ) Notice: Subject to any disclaimer, the term of this patent is extended or adjusted under 35 U.S.C. 154(b) by 0 days.

(21) Appl. No.: 09/947,626

(22) Filed: Sep. 6, 2001

(51) Int. Cl.[7] .............................. G02F 1/53; G02F 1/15; G02F 1/00; C07D 241/46
(52) U.S. Cl. ...................... 359/273; 359/265; 544/347; 252/583
(58) Field of Search ................. 359/273, 265, 359/275, 272; 252/583, 582; 544/347

(56) References Cited

U.S. PATENT DOCUMENTS

| | | | |
|---|---|---|---|
| 4,855,161 A | 8/1989 | Moser et al. ............... 427/108 |
| 5,124,080 A * | 6/1992 | Shabrang et al. ........... 252/583 |
| 5,277,986 A | 1/1994 | Cronin et al. ............... 428/432 |
| 5,470,673 A | 11/1995 | Tseung et al. ............... 429/44 |
| 5,471,338 A | 11/1995 | Yu et al. ..................... 359/273 |
| 5,471,554 A | 11/1995 | Rukavina et al. ........... 385/131 |
| 5,598,293 A | 1/1997 | Green ......................... 359/275 |
| 5,812,300 A | 9/1998 | Coleman ..................... 359/265 |
| 5,825,526 A | 10/1998 | Bommarito et al. ........ 359/265 |
| 6,355,125 B1 * | 3/2002 | Tahon et al. ................ 156/99 |

* cited by examiner

*Primary Examiner*—Georgia Epps
*Assistant Examiner*—Tim Thompson
(74) *Attorney, Agent, or Firm*—Duane Morris, LLP

(57) ABSTRACT

A flexible electrochromic device is disclosed, the device including a flexible substrate with at least one electrically conductive surface, and an electrochromic layer comprising a perfluorosulfonated anionic polyelectrolyte and a metal oxide, the electrochromic layer deposited on a conductive surface of the flexible substrate, wherein the device is capable of being deformed and returned to "flatness" in an undamaged state.

8 Claims, 2 Drawing Sheets

FLEXIBLE ELECTROCHROMIC DEVICES

FIELD OF THE INVENTION

This invention relates to the production of flexible electrochromic devices using electrically conductive flexible substrates and common manufacturing techniques.

BACKGROUND OF THE INVENTION

An electrochromic material undergoes a reversible color change upon the adsorption and desorption of small cations. This property can be exploited to fabricate a device that changes color upon the application of a voltage potential.

A typical electrochromic device comprises an electrochromic layer and an ion storage layer sandwiched between two conducting substrates, at least one of which is transparent. Optionally, the electrochromic layer and the ion storage layer can be separated by an ion-conducting electrolyte layer. Optical properties of the electrochromic device change when ions (e.g., hydrogen ions or lithium ions) intercalated within the structure of the ion-storage layer are removed and interposed within the structure of the electrochromic material in response to an electric potential applied to the conductive substrates. Ions are removed and returned to the ion-storage layer by reversing the polarity of the applied potential, thereby returning the electrochromic device to its original optical state.

The electrochromic layer and the ion storage layer are similar in that they both adsorb and desorb mobile ions in response to an applied electric field. A simple model for understanding electrochromic devices assumes that the electrochromic layer colors and clears during ion adsorption/desorption, while the ion storage layer remains transparent. However, practical electrochromic devices can be made if the ion storage layer colors as well. For example, if the electrochromic layer cycles from clear to color upon ion adsorption (e.g. tungsten oxide), and the ion storage layer cycles from clear to color upon ion desorption (e.g. nickel oxide), the overall devices will cycle from clear to color. If the electrochromic layer cycles from clear to blue upon ion adsorption (e.g. tungsten oxide), and the ion storage layer cycles from clear to yellow upon ion adsorption (e.g. vanadium oxide), the overall device will cycle from blue to yellow. Numerous combinations are possible.

Furthermore, if the ion-conducting electrolyte layer is opaque and the electrochromic layer cycles from clear to blue, the entire device will cycle from blue to the color of the ion-conducting electrolyte layer, regardless of the coloration of the ion storage layer.

The construction of an electrochromic device typically involves coating electrochromic material onto a transparent, conductive substrate. If the transparent, conductive substrate comprises glass, there are several proven coating methods available. These include evaporation deposition (Green, U.S. Pat. No. 5,598,293) and electro-deposition (Tseung et. al., U.S Pat. No. 5,470,673). Of particular advantage and commercially available utility is the coating of a transition metal alkoxide from an alcoholic solution (Moser et al., U.S. Pat. No. 4,855,161), followed by heating in excess of 200° C. Processes involving the coating from alcoholic solutions feature good uniform coverage, low capital investment, and low chemical toxicity.

An electrochromic device comprising flexible plastic substrates would have advantages over electrochromic devices comprising glass substrates. These advantages include light weight, durability, shapability and low cost. However, the known processes of coating from alcoholic solutions fail on commercially available electrically conductive plastic substrates. First, plastic substrates cannot tolerate high processing temperatures without serious degradation. Second, commercially available plastic substrates with conductive coatings often have a thin non-conductive layer applied to the conductive layer to promote conductor adhesion to the plastic substrate and to protect the conductive layer against scratching. This anti-scratching coating can cause poor adhesion of the electrochromic material deposited from alcoholic coating solutions. This is demonstrated in Examples 1, 2, and 4 below.

In U.S. Pat. No. 5,471,554, Rukavina et al. eliminate the anti-scratching coating by providing an adhesion layer between the plastic substrate and the transparent conductive layer. Yu et al., in U.S. Pat. No. 5,471,338 disclose similar technology. This is a relatively protracted process that still leaves the conductive layer subject to scratching during storage and subsequent processing.

In U.S. Pat. No. 5,812,300, Coleman describes an electrochromic device formed on a polyethylene terephthalate substrate by printing a silver flake/resin conductive layer and then an electrochrorniic layer coating from toluene. The silver flake conductive layer is not transparent, thus severely limiting the utility of the device. Furthermore, toluene is a harsh solvent that can deteriorate the optical clarity of the plastic conductive substrate.

In U.S. Pat. No. 5,277,986, Cronin et al. describe the incorporation of a fugitive organic material within the ethanolic coating solution to provide porosity of the electrochromic layer. This process requires temperatures in excess of that which plastic substrates can tolerate.

In U.S. Pat. No. 5,124,080, Shabrang et al. describe the use of perfluorosulfonic acid polymer as an ion-conducting electrolyte interposed between an electrochromic layer and an ion storage layer. Shabrang does not anticipate that incorporating perfluorosulfonic acid polymer into the electrochromic layer or the ion storage layer would be particularly advantageous for coating on plastic substrates.

In U.S. Pat. No. 5,825,526, Bommarito et al. describes vacuum deposition of electrochromic metal oxides on flexible transparent substrates, followed by a topcoat comprising a perfluoroamide. Forming an electrochromic layer of sufficient porosity and thickness on plastic substrates by means of vacuum deposition is difficult and expensive.

SUMMARY OF THE INVENTION

Glass electrochromic devices have not achieved broad commercial acceptance in architectural, automotive or eyewear applications, due to practical limitations. First, glass electrochromic devices can be prohibitively expensive to manufacture. Second, glass electrochromic devices cannot function the decades required for architectural and automotive applications. With each cycle, an electrochromic device suffers a minute but cumulative deterioration in performance, due to the accumulation of an irreversible colored "bronze" and trapped gas. Third, glass electrochromic devices are too heavy for eyewear applications and can also shatter to dangerous shards upon impact of a foreign object.

Plastic electrochromic devices address these limitations. Manufacturing costs are controlled by low capital requirements and high throughput. For example, in accordance with the present invention, an electrochromic layer or an ion storage layer could be coated on a continuous wide web of electrically conductive polyethylene terephthalate film at a rapid rate. The layers could then be laminated together using an adhesive ion conducting electrolyte. If this laminated film is applied to architectural and automotive glazing, the film could be replaced if its performance deteriorates over time. If the laminated film is applied to polycarbonate, or if the electrochromic device included polycarbonate coated directly, the electrochromic device would be light and safe enough for eyewear.

The present invention provides a composition of an electrochromic layer which coats uniformly from an alcoholic solution onto electrically conductive, flexible plastic, metal or fabric substrates which require low processing temperatures. This composition comprises a perfluorosulfonated anionic polyelectrolyte and a metal oxide selected from the group consisting of tungsten oxide, molybdenum oxide, niobium oxide, vanadium oxide, nickel oxide, cerium oxid titanium oxide, copper oxide, chromium oxide, rhodium oxide, manganese oxide, ruthenium hydroxide, osmium hydroxide, iridium oxide and mixtures thereof.

The present invention further provides a composition of an ion storage layer which coats uniformly from an alcoholic solution onto electrically conductive, flexible plastic, metal or fabric substrates and which require low processing temperatures. This composition comprises a perfluorosulfonated anionic polyelectrolyte and a metal oxide selected from the group consisting of tungsten oxide, molybdenum oxide, niobium oxide, vanadium oxide, nickel oxide, cerium oxide, titanium oxide, copper oxide, chromium oxide, rhodium oxide, manganese oxide, ruthenium hydroxide, osmium hydroxide, iridium oxide and mixtures thereof.

The metal substrate may be made of any electrically conductive metal or metal alloy, such as stainless steel, steel, nickel, aluminum, iron, copper, gold, silver, platinum, palladium, indium, tin and chromium.

The present invention further provides the means to fabricate electrochromic devices with the advantages of light weight, durability and flexibility.

DETAILED DESCRIPTION OF THE INVENTION

The present invention provides a composition of an electrochromic layer which coat uniformly from an alcoholic solution onto electrically conductive, flexible plastic, metal or fabric substrates which require low processing temperatures. This composition comprises a perfluorosulfonated anionic polyelectrolyte and a metal oxide selected from the group consisting of tungsten oxide, molybdenum oxide, niobium oxide, vanadium oxide, nickel oxide, cerium oxide titanium oxide, copper oxide, chromium oxide, rhodium oxide, manganese oxide, ruthenium hydroxide, osmium hydroxide, iridium oxide and mixtures thereof.

Figure 1:
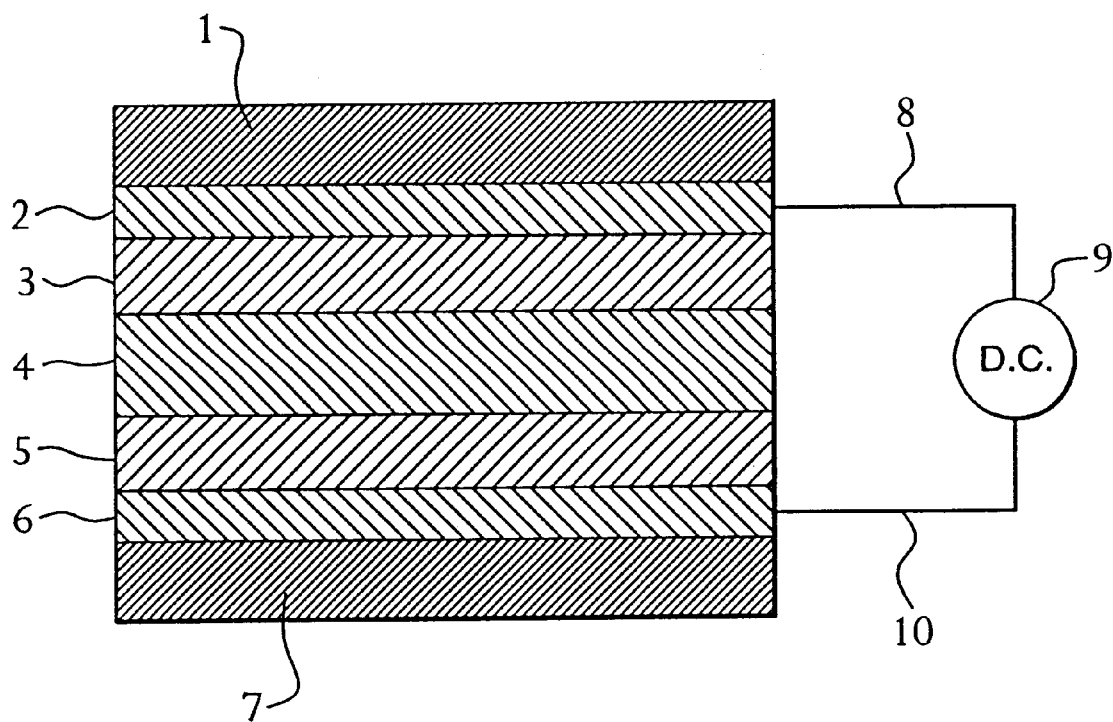
FIG. 1 is a cross-sectional view of the various layers of an embodiment of the present invention, the layers being deposited on polyethylene terephthalate film.

Referring now to FIG. 1, there is shown a flexible electrochromic device according to the present invention that includes transparent polyethylene terephthalate substrate 1 and transparent polyethylene terephthalate substrate 7. Onto polyethylene terephthalate substrate 1 is deposited conducting layer 2 of indium tin oxide; onto polyethylene terephthalate substrate 7 is deposited conducting layer 6 of indium oxide. Polyethylene terephthalate coated with indium/tin oxide is commercially available.

Electrochromic layer 3 comprising an electrochromic metal oxide and a perfluorosulfonated anionic polyelectrolyte is formed on layer 2 from an ethanolic solution using a dipping process to be described below. It should be understood that this dipping process is not critical in the present invention and that the electrochromic layer can be formed as desired.

Ion storage layer 5 comprising a metal oxide and a perfluorosulfonated anionic polyelectrolyte is formed on layer 6 from an ethanolic solution using a dipping process to be described below. It should be understood that this dipping process is not critical in the present invention, and that the ion storage layer can be formed as desired.

Ion conducting layer 4 comprising a perfluorosulfonated anionic polyelectrolyte is formed on layer 5 using a dipping process to be described below, and laminated to layer 3. It should be understood that this dipping process is not critical in the present invention and that the ion inducting layer can be formed as desired. It should be understood that the composition and method of application of layer 4 and layer 5 is not critical in the present invention and that alternate art can be used as desired.

From a direct current power supply 9, electrical connection 8 is made to indium tin oxide layer 2, and electrical connection 10 is made to indium tin oxide layer 6.

Figure 2:
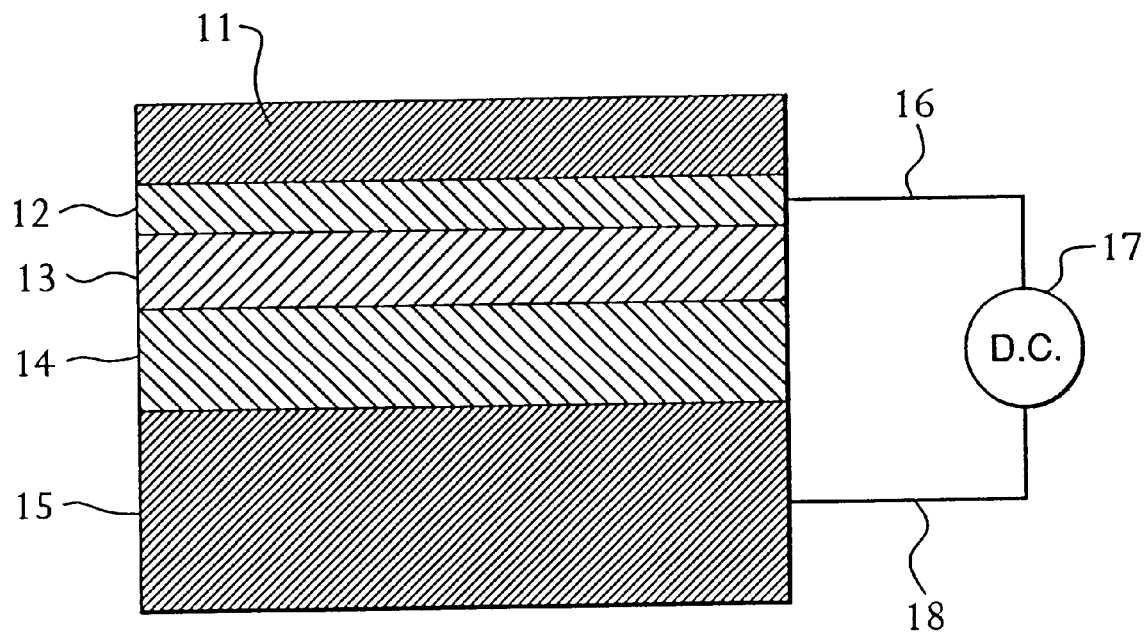
FIG. 2 is a cross-sectional view of the various layers of another embodiment of the present invention, incorporating stainless steel foil.

Referring now to FIG. 2, there is shown a flexible electrochromic device according to the present invention that includes transparent polyethylene terephthalate substrate 11 and flexible stainless steel substrate 15. Onto polyethylene terephthalate substrate 11 is deposited conducting layer 12 of indium tin oxide. Polyethylene terephthalate coated with indium tin oxide is commercially available.

Electrochromic layer 13 comprising an electrochromic metal oxide and a perfluorosulfonated anionic polyelectrolyte is formed on layer 12 from an ethanolic solution using a dipping process to be described below. It should be understood that this dipping process is not critical in the present invention and that the electrochromic layer can be formed as desired.

Ion conducting layer 14 comprising a perfluorosulfonated anionic polyelectrolyte is formed on layer 15 using a dipping process to be described below, and laminated to layer 13. It should be understood that the composition and method of application of layer 14 is not critical in the present invention and that alternate art can be used as desired.

From a direct current power supply 17, electrical connection 16 is made to indium tin oxide layer 12, and electrical connection 18 is made to stainless steel layer 15.

The limitations of the prior art and the utility of this invention are illustrated by the allowing examples.

EXAMPLE 1

Example 1 demonstrates that a commercially available coating solution will produce an electrochromic electrode from a glass substrate but will not produce an electrochromic electrode from a plastic substrate.

Tungsten (VI) Ethoxide, approximately 5 wt. % in ethanol, from the VWR Scientific Company was used as a coating solution.

A 25 mm×75 mm×1 mm soda-lime glass substrate (ITO/glass), coated one side only with indium tin oxide, was used.

A 25 mm×75 mm×2 mm clear polycarbonate substrate coated on one side with gold was used.

A 150 mm×150 mm×0.2 mm polyethylene terephthalate film (ITO/PET), coated on one side only with indium tin oxide, was used. From this was cut a 25 mm×75 mm×0.2 mm substrate.

All three substrates were measured to have an electrical resistance on one side of about 17 ohms/square.

Each substrate was dip-coated with Tungsten (VI) Ethoxide by the following method: A motorized apparatus was constructed that could withdraw a cotton thread at a uniform rate of 38 mm/minute. To the end of this thread was attached a metal clip. The thread and attached clip were fed through an iron ring attached to a ring stand so that the thread stretched down vertically under the weight of the clip. At the base of the ring stand was placed a high-form beaker filled with 5 wt % Tungsten (VI) Ethoxide in ethanol to a depth of about 37.5 mm. The clip was attached to a 25 mm side of the substrate, and the substrate hung vertically in the coating solution so that a substrate area of about 25 mm×37.5 mm was immersed. The substrate was allowed to stand in the solution for 30 seconds to assure good wetting. The motorized apparatus was then engaged, and the substrate was withdrawn from the coating solution at the rate of 38 mm/minute. Once the substrate cleared the lip of the beaker, it was hung suspended over the beaker for about 1 minute. The coated substrate was then removed from the clip and heated for 15 minutes in a 110° C. oven. This resulted in 25 mm×75 mm substrates of which a 25 mm×37.5 mm area was coated.

An electrode was tested for electrochromatic behavior in the following manner: A transparent high-form beaker was filled to a depth of approximately 25 mm with 0.5 N sulfuric acid into this beaker was placed a 25 mm×75 mm stainless steel mesh, to act as a counter electrode, and the electrode under test. The electrodes were stood on the 25-mm edge, in parallel, approximately 1 mm from each other. The electrode under test had the coated side immersed, and the coated side facing the stainless steel mesh. Approximately 25 mm×25 mm of the coated surface was immersed in the 0.5 N sulfuric acid. Electrical connection was made to the top of each electrode through a double-pole, double-throw (DPDT) switch, so that a 1.5 volt potential could be applied to the electrodes, and the polarity reversed by means of the DPDT switch. Applying a voltage potential, then reversing the polarity with the DPDT switch, allowed visible detection of a reversible electrochromic effect. For example, upon making an electrochromic electrode the cathode, the immersed portion of an electrochromic electrode could turn blue.

Each of the three coated electrodes was tested in turn, with the following result:

| Substrate | Electrochromic Behavior |
| --- | --- |
| ITO/glass | visible, reversible electrochromic effect |
| gold/polycarbonate | no visible electrochromic effect |
| ITO/PET | no visible electrochromic effect |

EXAMPLE 2

Example 2 demonstrates that an ethanolic tungstic acid solution, a commonly used solution to produce electrochromic electrodes, will produce an electrochromic electrode from a glass substrate but will not produce an electrochromic electrode from a plastic substrate.

Example 2 was carried out identically to Example 1, except that an ethanolic tungstic acid coating solution was utilized. The coating solution was prepared in the following manner:

A 250 mL Erlenmeyer flask was equipped with a stirring bar and set in a room-temperature water bath on a magnetic stirrer. The apparatus was held in place by a ring stand and clamps. All subsequent operation took place behind a transparent safety shield to protect against eruptions. Into the Erlenmeyer flask was introduced about 40 g of reagent grade 30 weight % aqueous hydrogen peroxide. The hydrogen peroxide was stirred and permitted to come to equilibrium with the water bath. Over the next 20 minutes, elemental tungsten powder of approximately 10 micron particle size was added to the hydrogen peroxide. A vigorous reaction ensued, and within about 120 minutes the tungsten was digested. The flask was removed from the bath, and platinum gauze inserted in the solution to remove excess peroxide. The flask was covered and allowed to stand overnight with the gauze in place. The following day, the gauze was removed, and to the beaker was added about 150 g of neat ethanol. After mixing, the solution was filtered through fluted filter paper into a glass bottle. Upon standing for one week, the solution changed from a translucent, slightly yellow solution to a deeper "straw" yellow. This solution was about 5 wt % tungstic acid solution in essentially ethanol.

This ethanolic tungstic acid solution was substituted for the Tungsten (VI) Ethoxide solution of Example 1, with the following results:

| Substrate | Electrochromic Behavior |
| --- | --- |
| ITO/glass | visible, reversible electrochromic effect |
| gold/polycarbonate | no visible electrochromic effect |
| ITO/PET | no visible electrochromic effect |

EXAMPLE 3

Example 3 demonstrates that the addition of a perflourosulfonated anionic polyelectrolyte to an ethanolic tungstic acid solution results in a coating solution that will produce an electrochromic electrode from a plastic substrate.

Example 3 was conducted identically to Example 2, except that the coating solution was prepared in this manner.

A 5 wt. % solution of perfluorosulfonated anionic polyelectrolyte in alcohol, obtained from Aldrich Chemical of Milwaukee Wis. and described as a 5% solution of Nafion® resin, was used as received. Nafion is a registered trademark of DuPont. About 14 g of the perfluorosulfonated anionic polyelectrolyte solution was mixed with about 21 grams of the tungstic acid coating solution of Example 2.

On all three substrates, the above coating solution produced transparent coatings of about 3000 angstrom thickness on the conductive side. Surprisingly, the solution did not coat the non-conductive side of the plastic substrates, thus eliminating the need to wipe this side clean before testing. The coated substrates were tested for electrochromic behavior, with the following results:

| Substrate | Electrochromic Behavior |
| --- | --- |
| ITO/glass | visible, reversible electrochromic effect |
| gold/polycarbonate | visible, reversible electrochromic effect |
| ITO/PET | visible, reversible electrochromic effect |

EXAMPLE 4

Example 4 demonstrates the usefulness of the lithium cation in the present invention. It also demonstrates the viability of a non-aqueous electrolyte.

The tungstic acid solution of Example 2 was combined with the 5 wt. % solution of perfluorosulfonated anionic polyelectrolyte of Example 3 according to the following table to produce coating solutions A through F.

| Coating Solution | Tungstic Acid | Perfluorosulfonated Anionic Polyelectrolyte |
| --- | --- | --- |
| A | 25.0 g | 0.0 g |
| B | 22.5 g | 2.5 g |
| C | 20.0 g | 5.0 g |
| D | 17.5 g | 7.5 g |
| E | 15.0 g | 10.0 g |
| F | 12.5 g | 12.5 g |

Six 25 mm×75 mm×0.2 mm TO/PET substrates were prepared; these were also labeled A through F. In turn, each substrate was dip-coated in its corresponding coating solution using the apparatus and method described in Example 1. Each substrate was tested for electrochromic behavior using the apparatus and method of Example 1, with two exceptions. The liquid electrolyte was 1 M lithium perchlorate in propylene carbonate instead of 0.5 M sulfic acid. The applied voltage was 3.0 V, not 1.5V. The following results were observed:

| Substrate | Electrochromic Behavior |
| --- | --- |
| A | No observed electrochromic effect |
| B | visible, reversible electrochromic effect |
| C | visible, reversible electrochromic effect |
| D | visible, reversible electrochromic effect |
| E | visible, reversible electrochromic effect |
| F | visible, reversible electrochromic effect |

EXAMPLE 5

Example 5 demonstrates the usefulness of this invention in fabricating a counter electrode.

Two electrodes were prepared by the identical method used to produce electrode E of Example 4. The substrates were tested for electrochromic behavior using the apparatus and method of Example 4, with one exception. While one electrode was installed in the apparatus as the electrochromic electrode under test, the second electrode was installed as the counter electrode in place of the stainless steel electrode.

Upon making the first electrode the cathode, the immersed portion of this electrode turned blue and the immersed portion of the second electrode visibly cleared. Upon reversing voltage polarity and making the first electrode the anode, the immersed portion of the first electrode visibly cleared, and the immersed portion of the second electrode turned blue.

EXAMPLE 6

Example 6 demonstrates the usefulness of the molybdenum oxide as the electrochromic metal oxide in the present invention.

A molybdenum oxide/ perfluorosulfonated anionic polyelectrolyte coating solution was prepared in the following manner:

Into a 50 mL beaker was placed about 4 g of 30 wt. % hydrogen peroxide. To this was slowly added about 1g of elemental molybdenum powder of particle size less than 5 microns. The reaction was very exothermic. The molybdenum was digested, and the contents of the beaker dried to a dark blue molybdenum oxide powder overnight. To this powder was added 20 mL of absolute ethanol, which dissolved the powder resulting in a dark blue solution of about 3.5 wt. % solids.

A coating solution was prepared by combining about 3 g of the dark blue solution with about 2 grams of the 5 wt. % solution of perfluorosulfonated anionic polyelectrolyte in alcohol described in Example 3. The coating solution was placed in a 10 mL glass vial.

The motorized apparatus described in Example 1 was employed for dip coating. A 10 mm×75 mm×0.2 mm PET/ITO piece was placed on the clip. It was immersed in the coating solution for about 30 seconds, and withdrawn at 38 cm/minute. Once the substrate cleared the lip of the vial, it was hung suspended over the beaker for about 1 minute. The coated substrate was then removed from the clip and heated for 15 minutes in an 110° C. oven. This resulted in a 10 mm×75 mm substrate of which about a 10 mm×37.5 mm area was coated.

The substrate was tested for electrochromic behavior using the apparatus and method of Example 1, with two exceptions. The liquid electrolyte was 1M lithium perchlorate in propylene carbonate instead of 0.5N sulfuric acid. The applied voltage was 3.0V, not 1.5V.

The substrate demonstrated a reversible electrochromic effect, cycling from transparent to light blue.

EXAMPLE 7

Example 7 describes a simple flexible electrochromic device which cycles from transparent to blue.

A 75 mm×25 mm electrochromic electrode was prepared by the identical method used to produce electrode E of Example 4. A 75 mm×25 mm PET/ITO substrate was used as a counter electrode. A few drops of 1M lithium perchlorate in propylene carbonate was placed on the ITO side of the PET/ITO substrate. The coated side of the electrochromic electrode was manually pressed onto the ITO side of the PET/ITO substrate, with a slight offset to allow electrical connection. This created a flexible, flat electrochromic device.

The device was connected to 1.5V, through a DPDT switch. Upon application of the voltage and reversal of polarity by means of the switch, the flexible electrochromic device cycled from transparent to blue.

EXAMPLE 8

Example 8 describes a simple flexible electrochromic device which cycles from white to blue. This device utilizes a metal counter electrode, and an opaque ion-conducting layer.

A 75 mm×25 mm electrochromic electrode was prepared by the identical method used to produce electrode E of Example 4. A 75 mm×25 mm piece of aluminum foil was used as a counter electrode. Porous white filter paper was soaked in 1M lithium perchlorate in propylene carbonate. This filter paper was placed on the aluminum foil. The coated side of the electrochromic electrode was manually pressed onto the filter paper, with a slight offset to allow eletrical connection. This created a flexible, flat electrochromic device.

The device was connected to 3.0V, through a DPDT switch. Upon application of the voltage and reversal of polarity by means of the switch, the flexible electrochromic device cycled from white to blue.

While this invention has been described in terms of exemplary embodiments, it is not limited thereto. Rather, the appended claims should be construed broadly to include other variants and embodiments of the invention which may be made by those skilled in the art without departing from the scope and range of equivalents of the invention.

We claim:

1. A flexible electrochromic device comprising:
   (a) a flexible substrate with at least one electrically conductive surface; and
   (b) an electrochromic layer comprising a perfluorosulfonated anionic polyelectrolyte and a metal oxide, said electrochromic layer deposited on a conductive surface of the flexible substrate, wherein said device is capable of being deformed and returned to flatness in an undamaged state.

2. The flexible electrochromic device as recited in claim 1, wherein said flexible substrate is metal.

3. The flexible electrochromic device as recited in claim 2, wherein the metal is selected from the group consisting of stainless steel, steel, nickel, aluminum, iron, copper, gold, silver, platinum, palladium, indium, tin, and chromium.

4. The flexible electrochromic device as recited in claim 1, wherein said flexible substrate is plastic.

5. The flexible substrate as recited in claim 4, wherein the plastic is deposited on at least one side with an electrically conductive layer.

6. The flexible electrochromic device as recited in claim 1, wherein the flexible substrate is polyethylene terephthalate.

7. The flexible electrochromic device as recited in claim 6, wherein the polyethylene terephthalate is deposited on one side with indium tin oxide.

8. The flexible electrochromic device as recited in claim 1, wherein said flexible substrate is fabric.

* * * * *